(12) United States Patent
Sinnott

(10) Patent No.: US 10,127,451 B1
(45) Date of Patent: Nov. 13, 2018

(54) METHOD OF DETECTING AND QUANTIFYING SUN-DRYING CROPS USING SATELLITE DERIVED SPECTRAL SIGNALS

(71) Applicant: Peter Cecil Vanderbilt Sinnott, Asheville, NC (US)

(72) Inventor: Peter Cecil Vanderbilt Sinnott, Asheville, NC (US)

( * ) Notice: Subject to any disclaimer, the term of this patent is extended or adjusted under 35 U.S.C. 154(b) by 0 days.

(21) Appl. No.: 15/786,504

(22) Filed: Oct. 17, 2017

Related U.S. Application Data

(60) Provisional application No. 62/488,896, filed on Apr. 24, 2017.

(51) Int. Cl.

| | |
|---|---|
| *G06K 9/00* | (2006.01) |
| *G06K 9/20* | (2006.01) |
| *G01N 21/31* | (2006.01) |
| *B64G 1/10* | (2006.01) |
| *G06Q 50/02* | (2012.01) |

(52) U.S. Cl.
CPC ....... *G06K 9/00657* (2013.01); *B64G 1/1021* (2013.01); *G01N 21/31* (2013.01); *G06K 9/2018* (2013.01); *B64G 2001/1028* (2013.01); *G06Q 50/02* (2013.01)

(58) Field of Classification Search
None
See application file for complete search history.

(56) References Cited

U.S. PATENT DOCUMENTS

| | | | | | |
|---|---|---|---|---|---|
| 7,058,197 | B1* | 6/2006 | McGuire | ............ | G06K 9/00657 |
| | | | | | 382/100 |
| 7,916,898 | B2* | 3/2011 | Anderson | ............ | A01B 69/008 |
| | | | | | 250/334 |
| 9,058,633 | B2* | 6/2015 | Lindores | ................ | G06Q 10/06 |
| 9,131,644 | B2* | 9/2015 | Osborne | ................ | A01G 7/00 |
| 9,202,252 | B1* | 12/2015 | Smith | ................ | G06Q 50/02 |
| 2011/0320229 | A1* | 12/2011 | Stehling | ................ | G06Q 10/04 |
| | | | | | 705/7.12 |
| 2018/0189564 | A1* | 7/2018 | Freitag | ................ | A01G 22/00 |

FOREIGN PATENT DOCUMENTS

CN     103440420     * 12/2013

* cited by examiner

*Primary Examiner* — Nancy Bitar

(57) ABSTRACT

The unique methodology and utility seeking patient protection in this application is using satellite imagery to quantify and derive harvest statistics of sun-drying crops.

High resolution imagery can be used to geospatially define known coffee drying basins however it is impractical for continuous observation as it is costly and infrequent.

The geospatially defined regions of interests of coffee drying basins can be matched with more frequent, lower resolution, multispectral satellite imagery (such as Sentinel-2). The signals can be tested against the known spectral signatures of washed and unwashed coffee to determine whether or not each pixel contains coffee.

The result will yield a classified region of interest which can be used to determine the quantity of drying coffee and the washed to unwashed ratio of a harvest. With regular monitoring across multiple temporal scenes the harvest's seasonality and historical change can be derived.

3 Claims, 4 Drawing Sheets

METHOD OF DETECTING AND QUANTIFYING SUN-DRYING CROPS USING SATELLITE DERIVED SPECTRAL SIGNALS

CROSS REFERENCE TO RELATED APPLICATIONS

The present application claims the benefit of provisional patent application Ser. No. 62/488,896, filed 2017 Apr. 4 by the present inventor.

TECHNICAL FIELD

The present invention relates to the remote sensing of agriculture.

BACKGROUND—PRIOR ART

The following is a tabulation of some prior art that presently appears relevant:

U.S. Patent application Publications

| Pat. No. | Kind Code | Publ. Date | Patentee |
|---|---|---|---|
| 0,234,691 | A1 | 2005 Oct. 20 | Singh et al. |
| 5,878,356 | A1 | 1999 Mar. 2 | Garrot |
| 0,101,239 | A1 | 2011 May 5 | Woodhouse et al. |
| 7,058,197 | B1 | 2006 Jun. 6 | McGuire et al. |

It is known in the prior art to employ satellite imagery for monitoring crops such as corn, sugar, wheat, soy, and others. Multispectral satellites measure frequencies of light across the electromagnetic spectrum, beyond what is perceivable to the human eye. With this imagery graphical indicators like the Normalized Difference Vegetation Index (NDVI) can be derived to assess for the presence of live vegetation. Materials can also be classified based on their unique spectral signature as different materials reflect light differently.

The Normalized Difference Vegetation Index (NDVI) is calculated using reflectance values satellites receive in the red and near-infrared (NIR) spectral bands. Chlorophyll, in healthy green-leaf vegetation, absorbs red wavelengths. Conversely, near-infrared wavelengths are reflected by a healthy plant's cellular structure. These two bands construct the NDVI which ranges from negative one to one. NDVI is calculated as follows:

$$NDVI=(NIR-red)/(NIR+red)$$

Water bodies (void of vegetative matter) have an NDVI value of negative one whereas forests have a positive NDVI value.

Several past patents have proposed using NDVI for crop prediction such as U.S. Pat. No. 0,234,691 (2005). This patent claims that the prediction model can be applied to any vegetable, fruit, grain, nut, legume, etc. ([0041]). For full-sun crops this method may be feasible. Corn is grown in full-sun so the reflectance values collected by a satellite are be reflected directly from the corn plant, the top layer of the given scene. For analysis of shade grown crops however, this method is incompatible as the reflectance values will be those of the outermost canopy layer and not necessarily of the crop under investigation.

Most coffee is shade grown. When applied over a coffee farm U.S. Pat. No. 0,234,691 would not provide any insightful information as to the health of the coffee plants but rather would just provide a loose indicator as to the health of the surrounding forest.

Most cultivated coffee is derived from only two Ethiopian-originating strains: *Arabica* and *Robusta*. This lack of genetic diversity within the specie's cultivation is why the crop is notably susceptible to disease. *Arabica* accounts for 70% of global production and grows best under shade. *Robusta* is more sun tolerant though is often shade grown. Coffee and its surrounding forest form part of an interdependent agroforestry system. Within a defined spatial environment many species exist. Although coffee may be the farmers focus, it is most certainly not spatially homogeneous like corn, sugar, soy, and other sun grown crops.

U.S. Pat. No. 0,234,691 (2005) extends beyond NDVI by deriving other indicators to gauge a region's growing suitability. The proposed method incorporates rainfall and soil moisture data to derive a yield estimate. These factors however would be largely uncorrelated to the coffee's yield should a disease such as Coffee Rust be effecting the coffee plants below the canopy. This method would be fooled as such a disease may directly increase the NDVI of the canopy layer; should the coffee plants be suffering from Coffee Rust more nutrients and moisture would be available for the surrounding trees making the system appear healthy based on top-level NDVI. Along with coffee, undetectable sub-canopy crops within the agroforestry ecosystem may include: pepper, cacao, and an array of others.

U.S. Pat. No. 7,058,197 (2006) is another NDVI dependent method claiming to be broad enough to monitor virtually any growing vegetation. This method first attempts to cluster regions based on each potential land cover within the area of interest. Next every individual pixel is classified according to its multispectral signature's highest probability likelihood. From each classified pixel an NDVI value is derived and from there a vegetation index value. As this derived vegetation value will change over time and season, the patent claims this method can be used for monitoring crop response zones and temporal cycles such as seasonality. Again this patent fails to account for the heterogeneous nature of an agroforest ecosystem. When coffee is planted usually only the sublayer is cleared and the upper canopy remains unaltered. Thus satellite imagery of a forested coffee farm will be very similar to that of a virgin forest. This method would be unable to classify coffee into a regional cluster. Even if defining areas under coffee cultivation into regional clusters was possible, the vegetation index would only be reflective of the tallest vegetative matter (most commonly trees) in the agroforestry system—not an effective means of monitoring the coffee below. For the same reasons. U.S. Pat. No. 0,214,984 (2009) also fails as a means for monitoring shade grown crops.

Even aerial based methods of remote sensing (such as UAVs and airplanes) are unable to monitor sub-canopy crops. U.S. Pat. No. 5,878,356 (1999) proposes collecting visual and infrared imagery with an Unmanned Aerial Vehicle for resource monitoring. This patent claims that with such imagery an Indo-Jackson Crop Water Stress Index can be derived to measure foliage temperature. With foliage temperature one can derive crop influencing factors such as soil moisture content, soil water matrix potential, and photosynthesis. While canopy-level reflectance readings may indicate properties such as soil moisture, this method fails to assess coffee health and disease variables such as Coffee Rust Disease and the Coffee Bean Borer. Both have a tremendous impact on coffee harvests globally. This patent relies too heavily on canopy derived indices which don't reflect the health of an entire agroforestry ecosystem. This method would also not be feasible for monitoring coffee on a large scale given the limitations of UAVs. This patent claims to addresses the costly nature of acquiring satellite imagery. Fortunately, much satellite imagery is now freely available for public use.

U.S. Pat. No. 0,101,239 (2011) combines multispectral and LIDAR imagery. LIDAR penetrates the vegetation to reflect a forest's true ground layer. LIDAR combined with reflectance readings from a forest's canopy can be combined to calculate biomass with a simple volumetric calculation.

A large forest biomass however may not correlate to a great expanse of coffee plants within the system and may correlate very little with the actual yield of these plants. Using this method a very tall and thick canopy layer would suggest a large biomass. As measurements are only taken at ground and canopy levels, there is no way to quantify medium height sub-canopy vegetation such as coffee. Coffee's biomass as a portion of an agroforestry system is very variable. New coffee may be planted under a very tall forest yielding a large biomass reading for the scene despite such small and unproductive coffee plants.

SUMMARY OF THE EMBODIMENTS

By classifying remotely sensed multispectral signals over areas where coffee is sun-dried, coffee harvest statistics can be derived.

Sun drying coffee may have two unique spectral signatures, washed or unwashed. Unwashed coffee dries while retaining the red outermost fruit encompassing the bean. Washed coffee dries after this fruity pulp layer is removed. The difference between the spectral signatures of washed and unwashed sun-drying coffee is most notable in the Near Infrared and Short Wave Infrared wavelengths.

With these two signatures defined, an algorithm can test the signals of each pixel of the multispectral image to determine the presence of matching band signatures and thus the presence of washed or unwashed coffee.

The algorithm may also test for the cloud obstruction. Cloudy pixels are masked when calculating regional statistics. Pixels classified as neither washed, unwashed, or cloud indicate areas where the drying basin is likely bare or insufficiently filled to classify.

The classification will take place over geospatially defined coffee drying basins. The method however is not limited to classifying over pre-defined regions of interest as classifying over unknown land-use is useful in mapping new areas of sun-drying activity.

Figure 1:
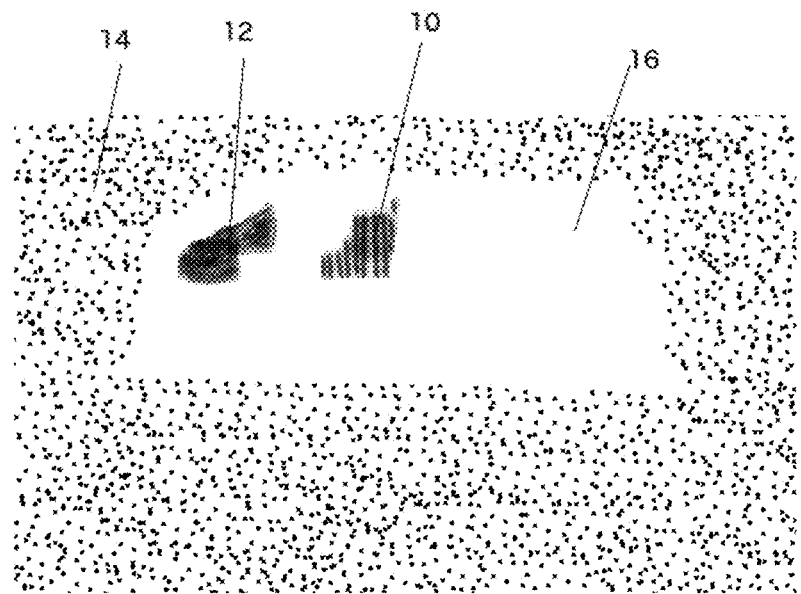
FIG. 1 illustrates a high-resolution satellite image rendered in visual light over a coffee estate sun-drying beans.

| Drawings - Reference Numerals | |
|---|---|
| 10 unwashed coffee | 12 washed coffee |
| 14 surrounding forest | 16 cleared land |
| 18 polygon edge | 20 polygon defined region of interest |
| 22 polygon border | 24 one low-resolution pixel |
| 26 classified washed coffee | 28 classified unwashed coffee |
| 30 classified 'no coffee' (bare basin) | 32 cropped pixel |
| 34 coffee bean | 36 silverskin and parchment of a coffee cherry |
| 38 pulp of a coffee cherry | 40 sample points of sun drying unwashed coffee |
| 42 best fit line | |

DETAILED DESCRIPTION OF SPECIFIC EMBODIMENTS

The present invention is a method of taking signals captured from an earth orbiting satellite and deriving the physical quantity of a harvested sun-drying crop within a defined region of interest. The present invention takes advantage of the remote sensing of visible, near-infrared, and short-wave radiation reflected from a region of interest in order to generate the initial raw data. The raw data is then converted to two vegetation indices (NDVI and NDWI). The indices and raw data is then classified.

While the present invention is described herein with reference to illustrative embodiments for particular applications for analyzing sun-drying coffee beans, it should be understood that the invention is not limited thereto. Those having ordinary skill in the art and access to the teachings provided herein will recognize additional modifications, applications, and embodiments within the scope thereof and additional fields in which the present invention would be of significant utility. This would most notably be recognized as modifying the methodology to detect for other sun-drying crops such as cacao and pepper.

The derived classification equations can be altered and adapted to detect for the presence of other sun-drying crops within a region of interest. The region of interest may be expanded beyond areas of known sun-drying activities as a means of mapping new areas of sun-drying activity.

The linear regression model used for classifying drying unwashed coffee beans may also be applied to other sun-dying fruits or beans and used as a means of determining dryness.

Overview of Remote Sensing in Agriculture

Technological advances in remote sensing, notably satellite image acquisition, has enabled new methods for quantifying, estimating, and assessing the health of and quantity of agricultural harvests on a global scale. Some of the data used is high-resolution visual imagery. High-resolution satellite imagery is generally considered to have a resolution at three squared meters or less per pixel. The image is rendered from three bands containing reflectance values of each of the primary colors. This imagery can be used for counting ships passing through a port, for example, a sign of economic activity.

Multispectral satellites collect light not only in the visual wavelengths, but also in wavelengths outside of the visual spectrum such as near-infrared, shortwave-infrared, thermal, and others. With multispectral imagery more complex analytics can be derived. The Normalized Difference Vegetation Index is calculated using an equation factoring in the visual red and the near-infrared bands of an image. NDVI is useful in detecting healthy live vegetation. This can be compared to historical images and harvest statistics to derive harvest yield change in sun-grown crops.

Overview of Coffee as a Shade-Grown Crop

Unlike corn, coffee is often grown under a forested canopy making direct detection of the plant unfeasible. Once picked however, coffee is sun dried for several days.

Figure 5:
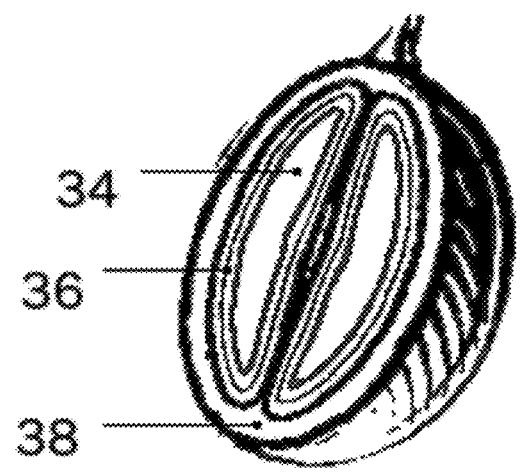
FIG. 5 shows the cross-section of a coffee cherry.

FIG. 5 shows the cross section of a coffee cherry. As coffee is a fruit, with just the inner seed (FIG. 5-34) becoming what we use to brew coffee, the fleshly fruit covering, or pulp. (FIG. 5-38) of the coffee is either first removed in a process known as washing or the entire cherry is dried without removing the pulp. The silverskin coating of the bean (FIG. 5-36) is not removed before either drying process.

During harvest season coffee farmers will sun-dry washed, unwashed, or a combination. As the washing process removes the pulp, the cherry's physical properties are altered. Washed and unwashed coffee have two unique spectral signatures.

Temporal Variation in Spectral Curves

Many objects have a spectral signature that is dynamic over time. An agricultural field starts as bare soil. As vegetation begins to emerge and fill the field there is a lowering of the red reflectance (due to increased chlorophyll) and an increase in near-infrared reflectance (due to increased cellular structure). The spectral curve of this agricultural site thus begins to take the signature of healthy green vegetation.

The dynamic nature of spectral curves also exists in the context of sun-drying beans. As unwashed coffee cherries dry, the water content decreases (decreasing NDWI) and the outer pulp of the cherry's cellular structure shrivels, increasing chlorophyll density (and increasing NDVI).

First Embodiment—Defining Region of Interest

Figure 2:
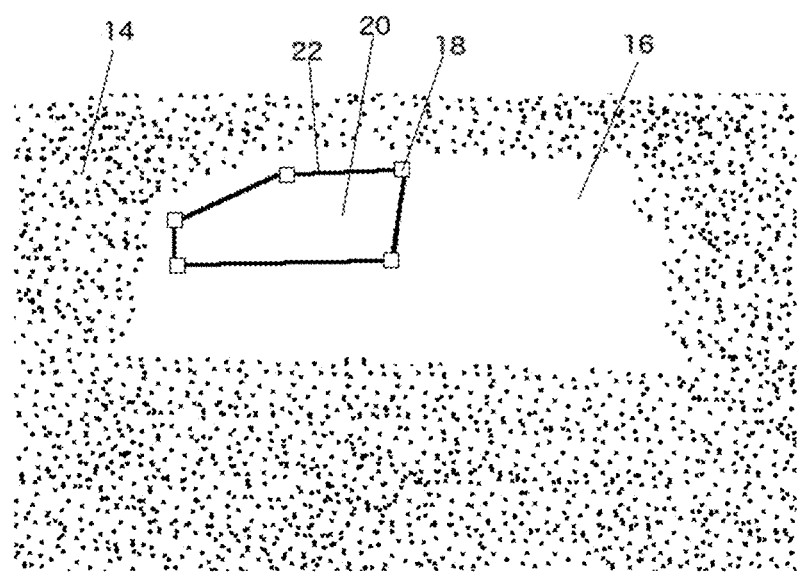
FIG. 2 illustrates defining a region of interest over an area where beans are sun-dried.

One embodiment of the procedure is illustrated in FIG. 1 and FIG. 2. FIG. 1 illustrates visual high resolution satellite imagery of a coffee estate. In the illustration one can see the dense forest 14 under which coffee is shade grown. A clearing in the forest 16 provides the necessary sun exposure to allow the coffee to sun-dry. In the drying area, during harvest season, one may observe both washed 12 and unwashed 10 coffee. In high-resolution imagery these two are visually distinct. Unwashed coffee 10 is darker than washed coffee 12.

Image acquisition at high resolution is expensive and temporally infrequent, limiting it as a practical means of continuous observation. It is useful however in defining regions of interests.

FIG. 2. Shows how a georeferenced region of interest is created by selecting points 18 along the edge of the drying basin, following its perimeter 22, to create a polygon 20 of the area in which coffee is sun-dried. From high resolution imagery one can determine the expanse of the region 22. The drying basin is often built of cement or packed dirt, distinct from its surroundings.

With a georeferenced region of interest defined 22, the polygon may be exported as a shapefile and the signals of a multispectral satellite image within may be assessed and classified.

Regions of interest can also be created by other means, such as recording ground points along a drying basin's perimeter 22 and manually building the polygon with GIS software.

Second Embodiment—Region of Interest Overlay

Low-resolution multispectral satellite imagery (at a resolution of 10 meters squared or more per pixel) is useful for monitoring harvest yields on a regular temporal scale. The resolution is sufficient for classification and the temporal scale frequent. The signals collected by the Sentinel 2 satellite contains the necessary frequencies outside of the visual light spectrum essential for calculating NDVI and NDWI.

The geospatially defined region of interest (FIG. 2.-22) can be used as an overlay to map which pixels are to be classified.

Figure 3:
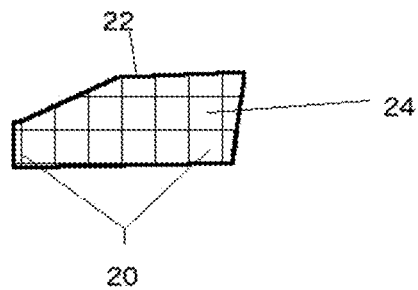
FIG. 3 shows the region of interest cropped and delineated to represent the pixilation of a lower resolution satellite image.

FIG. 3 shows the same region of interest 20 illustrated to the pixel resolution quality of a low-resolution multispectral satellite such as Sentinel-2 which captures multispectral imagery at a 10 meter squared resolution. In FIG. 3 each pixel 24 can be seen delineated as a square. For each pixel 24 the satellite obtains wavelength signals across the visual, near-infrared, and short-wave infrared frequencies.

Third Embodiment—Classification

For each pixel within the defined region of interest 20 a classification test is carried out using bands inside and out of the visual spectrum. The wavelengths collected by Sentinel-2 are broken into the following bands:

| Sentinel-2 Bands | Central Wavelength (µm) |
| --- | --- |
| B2—Blue | 0.490 |
| B3—Green | 0.560 |
| B4—Red | 0.665 |
| B5—Vegetation Red Edge | 0.705 |
| B6—Vegetation Red Edge | 0.740 |
| B7—Vegetation Red Edge | 0.783 |
| B8—NIR | 0.842 |
| B11—SWIR | 1.610 |

From these bands, first NDWI and NDVI are calculated:

NDWI=(Near Infrared Band 8−Short Wave Infrared Band 11)/(Near Infrared Band 8+Short Wave Infrared Band 11)

NDVI=(Near Infrared Band 8−Red Band 4)/(Near Infrared Band 8+Red Band 4)

NDVI and NDWI are amended to the dataset of each pixel. Tests are then performed to determine if the pixel contains either washed coffee, unwashed coffee, cloud coverage, bare drying basin (no coffee), or unknown substances.

Each pixel is compared to the spectral signature of unwashed coffee to test for the presence of unwashed coffee.

Is the recorded reflectance of the blue band (B2) greater than 31% the total of all visual bands?

Is: $B2/(B2+B3+B4)>31\%$

Is the reflectance of blue greater than the reflectance of green?

Is: $B2>B3$

Is near-infrared reflectance greater than visual red reflectance?

Is: $B8>B4$

Figure 6:
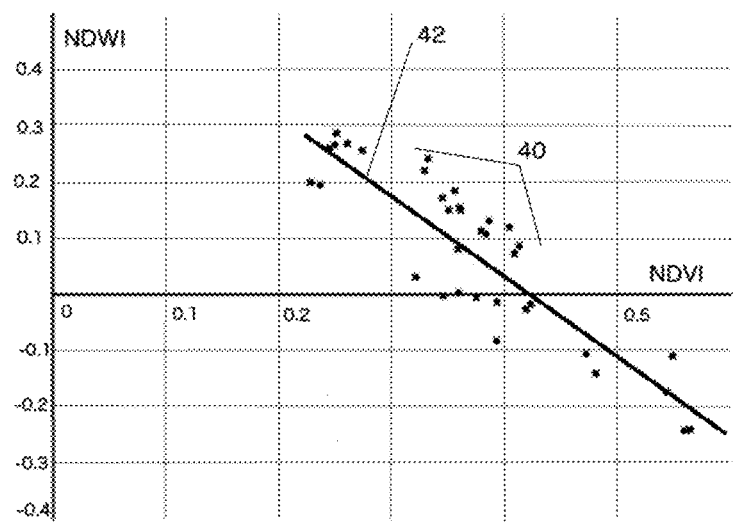
FIG. 6 shows a drying unwashed coffee cherry's Normalized Difference Water Index to Normalized Difference Vegetation Index relationship.
Figure 7:
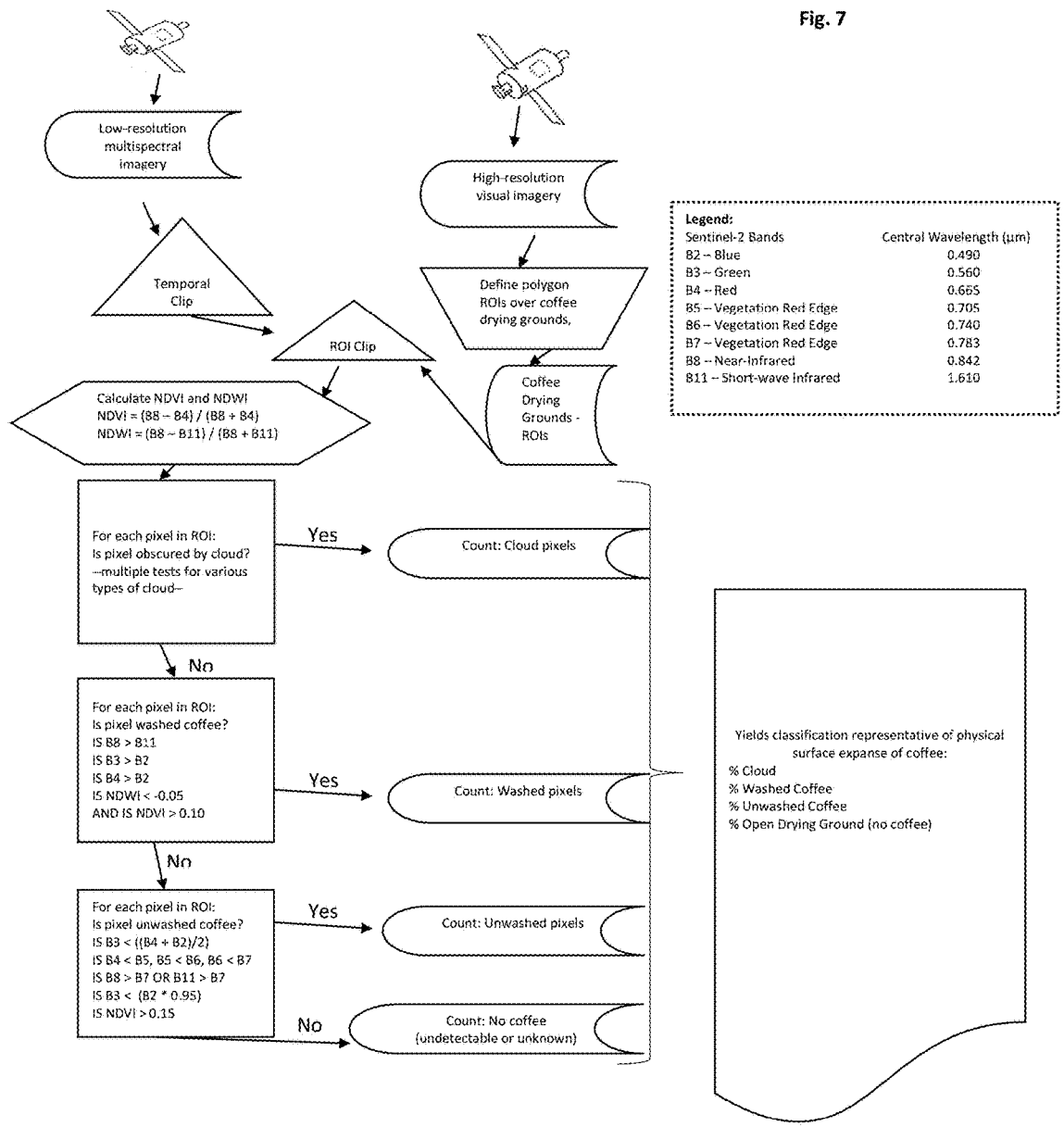
FIG. 7 shows a flowchart of the classification process.

Lastly, does the relationship between the pixel's NDVI and NDWI fall close to the defined regression illustrated in FIG. 6.-42. The margin of error can be adjusted by altering the b values of the equation (y=m*x+b) relative to standard deviation.

Is: NDWI>−1.5*NDVI+0.55 and

Is: NDWI<−1.5*NDVI+0.75

The pixel is classified as containing sun-drying unwashed coffee if it meets these tests.

In testing for the presence of washed coffee, a classification model testing the pixel's spectral signature is used. As the outer pulp of the coffee cherry 38 is already removed before drying, one cannot rely on the same NDVI to NDWI relationship as employed for testing unwashed coffee. In mapping a pixel as washed, the following tests are employed.

First NDVI is tested. As the bean is vegetative matter with chlorophyll reflecting high levels of near-infrared and low levels of the visual red light.

Is NDVI>0.1

NDWI of washed coffee will be less than zero as the pulp 38 has already been removed. Without this more short-wave infrared and less near-infrared is reflected.

Is NDWI<0

Visual bands are then tested using unwashed coffee's known spectral signature:

Is red reflectance greater than 36% of the combined visual bands?

Is $B4$ Red/($B2$ Blue+$B3$ Green+$B4$ Red)>36%

Is the red reflectance values greater than both that of blue and green?

Is $B4$ Red>$B3$ Green?

and

Is $B4$ Red>$B2$ Blue?

Washed coffee also reflects greater values of green than blue, so:

Is $B3$ Green>$B2$ Blue?

It is also important to test for cloud coverage which may obscure classification within the drying basin. In Sentinel-2 imagery, if cirrus or opaque clouds are present, a band called 'QA60' is amended to the dataset. To test for these clouds, the following suffices:

Is QA60>100.

If the test returns true, the pixel is classified as cloud.

A more complex cloud mask incorporating several bands can also be used:

Is (NDVI<0.4) AND (($B8/B3$)<1.2) AND (($B2/B11$)>0.70))

or

Is ($B8A$<1050) AND ($B8$<1200) AND ($B3$<2000) AND (NDVI<0.10))

or

Is (($B3+B8A$)>40000) AND ($B3<B2$) AND ($B4<B2$))

or

Is (QA60>25)

or

Is ($B8A$>4500)

The if/or statements allow for the testing of different types of clouds as different clouds have different spectral signatures based on their altitude, contents, and character.

Should each pixel classify as neither washed coffee, unwashed coffee, or cloud, it is tested for any traces of vegetative matter.

Is NDVI<0.09

If this test is true, it is confident to say that the basin contains little to no vegetative matter.

If this test fails however, the pixel is classified as unknown. Unknown pixels may be areas containing traces of drying coffee, but perhaps not enough to match with washed or unwashed coffee's spectral signature. Otherwise these pixels may be areas containing vegetative matter other than coffee.

Operation

Figure 4:
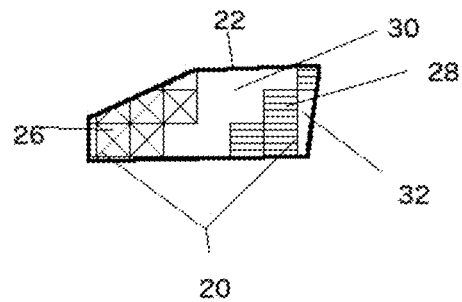
FIG. 4 shows the classified region of interest.

Using the scene from FIG. 1 one could expect a classification as illustrated in FIG. 4. Again the washed coffee 10 is classified as washed coffee 26, the unwashed coffee 12 as unwashed coffee 28, and the empty portions of the drying basin are classified as empty 30.

Some pixels will cover areas both inside and outside of the defined region of interest. These pixels are cropped. FIG. 4 illustrates cropped pixels 32. These pixels will contribute as fractions relative to their area within the region of interest 20 when calculating total area of drying coffee.

CONCLUSION, RAMIFICATIONS, AND SCOPE

The area of the resulting classification is totaled. Statistics are calculated such as the percentage of washed and unwashed coffee within a basin. Coffee yield figures are accurately derived based on the surface expanse of the dying coffee. When coffee dries the depth of the drying coffee is consistently kept at a minimal depth of just one bean to avoid rotting. Volume is thus easily calculated.

This method allows for the monitoring of coffee farms globally. Running this procedure across a sample of farms will be a strong indicator of regional or global coffee productivity levels.

This method is not limited to coffee. Any sun drying bean, fruit, or other vegetative matter may be classified and monitored simply by altering the classification algorithm according to the properties of the substance in question.

This method has been developed to a high level of usability. Satellite derived coffee harvest analytics have already been supplied to world leading green coffee service groups. Site specific analytics have also been back tested against multi-year ground data. Lastly, regional Brazilian yield figures have been accurately calculated using a database of sample Brazilian sample sites.

I claim:

1. A method of assessing a harvest of sun drying crops, comprising:
    capturing a multispectral satellite or an aerial image of a coffee estate sun-drying beans including areas where coffee is sun-dried;
    defining a geospatial region of interest within the image;
    calculating a Normalized Difference Vegetation Index and a Normalized Difference Water Index for each pixel within the geospatial region of interest;

testing each pixel within the geospatial region of interest for a reflectance value matching at least one spectral signature including washed or unwashed coffee dries;

classifying each pixel within the geospatial region of interest based on the spectral signature and the calculated Normalized Difference Vegetation Index and the Normalized Difference Water Index;

comparing temporal changes of the Normalized Difference Vegetation Index and the Normalized Difference Water Index for each classified pixel within the geospatial region of interest;

analyzing a harvest cycle and an amount of crop drying based on the spectral signature, the Normalized Difference Vegetation Index and the Normalized Difference Water Index for each of the classified pixel within the geospatial region of interest;

counting the classified pixels to monitor and quantify the amount of crop dying and the harvest cycle;

assessing the coffee estate sun-drying beans after monitoring and quantifying the amount of crop dying and the harvest cycle; and deriving a regional or global coffee productivity levels using the assessing of the coffee estate sun drying beans and comparing the productivity levels across a sample of farms.

2. The method according to claim 1 comprising:

testing and classifying each pixel against a correlation of decreasing Normalized Difference water Index and increasing Normalized Difference Vegetation Index as containing unwashed beans drying.

3. The method of claim 2, wherein the classification of each pixel includes areas both inside and outside of the geospatial region of interest.

* * * * *